United States Patent [19]

Knight et al.

[11] 4,042,459

[45] Aug. 16, 1977

[54] COMPOSITION OF MATTER AND PROCESS

[75] Inventors: John C. Knight, Kalamazoo Township, Kalamazoo County; Merle G. Wovcha, Kalamazoo, both of Mich.

[73] Assignee: The Upjohn Company, Kalamazoo, Mich.

[21] Appl. No.: 632,650

[22] Filed: Nov. 17, 1975

[51] Int. Cl.$^2$ .............................................. C07B 29/00
[52] U.S. Cl. .................................. 195/51 S; 195/112
[58] Field of Search ....................................... 195/51 S

[56] References Cited

U.S. PATENT DOCUMENTS 3,853,707   12/1974   Becher et al. ...................... 195/51 S

OTHER PUBLICATIONS

Schubert et al., 4:581-586 (1964).
Wang et al., Biochem. 2:1238-1243 (1963).

*Primary Examiner*—Alvin E. Tanenholtz
*Attorney, Agent, or Firm*—Roman Saliwanchik

[57] ABSTRACT

Novel compounds prepared by microbial transformation using novel mutants to selectively degrade steroids with or without 17-alkyl side chains of from 2 to 10 carbon atoms, inclusive. These compounds can be used as intermediates to make useful steroids.

40 Claims, No Drawings

COMPOSITION OF MATTER AND PROCESS

BACKGROUND OF THE INVENTION

The transformation of steroids by microorganisms has been widely studied and documented. Apparently, the earliest such work was by Mamoli and Vercellone in 1937, Ber. 70, 470 and Ber. 70, 2079. They disclosed the reduction of 17ketosteroids to 17β-hydroxysteroids by fermenting yeast. More recently, Peterson and Murray disclosed the 11α-hydroxylation of progesterone with the fungus Rhizopus nigricans; see, U.S. Pat. No. 2,602,769 (1952). Also recently, Kraychy et al. in U.S. Pat. No. 3,684,657 (1972) discloses the selective microbiological degradation of steroidal 17-alkyls be fermenting a steroid containing at least 8 carbons in the 17-alkyl side chain with Mycobacterium sp. NRRL B-3683 to prepare androst-4-ene-3,17-dione, androst-1,4-diene-3,17-dione, and 20α-hydroxymethyl-pregna-1,4-dien-3-one. Even more recently, Marsheck et al. in U.S. Pat. No. 3,759,791 (1973) disclose the selective microbiological preparation of androst-4-ene-3,17-dione by fermenting a steroid of the cholestane or stigmastane series containing at least 8 carbons in the 17-alkyl side chain with Mycobacterium sp. NRRL B-3805.

Compound III of the subject invention has been disclosed by Wang and Sih in 1963 (Biochem. 2: 1238–1243) as an intermediate in the degradation of androst-4-ene-17βol-3-one by Nocardia restrictus. The open ring form of compound 1, 7α-methyl:perhydroindanedione-(1,5)-[β-propyl alcohol-(4)], has been disclosed by Schubert et al. in 1964 (Steroids 4: 581–586) as an intermediate in the degradation of progesterone by Mycobacterium smegmatis.

BRIEF SUMMARY OF THE INVENTION

Mutants which are characterized by their ability to selectively degrade steroids with or without 17-alkyl side chains of from 2 to 10 carbon atoms, inclusive, and accumulate the following compounds in the fermentation beer:

3aα-H-4α-[3'-propanol]-7aβ-methylhexahydro-1,5-indandione hemiketal

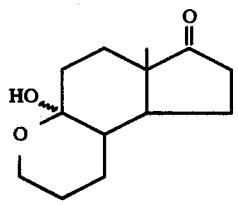

hereinafter referred to as Compound I:
3aα-H-4α-[3'-propanal]-5α-hydroxy-7aβ-methylhexahydro-1-indanone hemiacetal

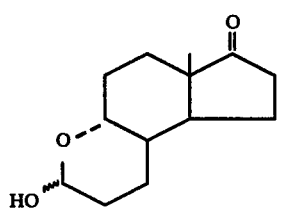

hereinafter referred to as Compound II;

3aα-H-4α-[3'-propionic acid]-5α-hydroxy-7aβ-methylhexahydro-1-indanone-δ-lactone

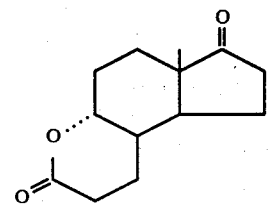

hereinafter referred to as Compound III; and,
3aα-H-4α-[3'-propanol]-5α-hydroxy-7aβ-methylhexahydro-1-indanone

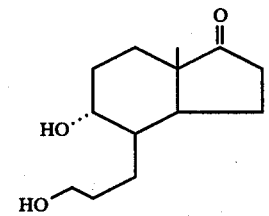

hereinafter referred to as Compound IV.

These mutants can be obtained from sterol-degrading microorganisms of the following genera by using the mutation procedures disclosed herein or other mutation procedures: Arthrobacter, Bacillus, Brevibacterium, Corynebacterium, Mycobacterium, Nocardia, Protaminobacter, Serratia, and Streptomyces. A preferred genus is Mycobacterium. Exemplary species of this genus are M. phlei, M. smegmatis, M. rhodochrous, M. mucosum, M. fortuitum, and M. butyricum. Specifically exemplified herein is a novel mutant microorganism, Mycobacterium fortuitum, NRRL B-8128, which is used to selectively degrade steroids with or without 17-alkyl side chain containing from 2 to 10 carbon atoms, inclusive, to the compounds I, II, III and IV. Examples of suitable steroids are sitosterols, cholesterol, stigmasterol, campesterol, and like steroids with 17-alkyl side chains of from 2 to 10 carbon atoms, inclusive, and androst-4-ene-3,17-dione, androsta-1,4-diene-3,17-dione, dehydroepiandrosterone, and testosterone. These steroids substrates can be in either the pure or crude form.

DETAILED DESCRIPTION OF THE INVENTION

The Microorganisms

Mutants which are characterized by their ability to selectively degrade steroids, as defined above, and accumulate compounds I, II, III and IV in the fermentation beer, can be obtained by mutating sterol-degrading microorganisms of the following genera: Arthrobacter, Bacillus, Brevibacterium, Corynebacterium, Mycobacterium, Nocardia, Protaminobacter, Serratia, and Streptomyces. Mycobacterium fortuitum, ATCC 6842, has been mutated, as disclosed herein, to give a novel laboratory mutant microorganism. The 1974 ATCC Catalogue discloses the following alongside the listing of ATCC 6842: "J.C. Cruz 2. Cold abscess. Acta Med. Rio de Janeiro 1:1 (1936). Medium 90 37C". M. fortuitum, ATCC 6842, degrades sterols non-selectively to small molecular weight compounds, e.g. $CO_2 + H_2O$.

Thus, this microorganism is not suitable as a selective steroid degrader.

Mutation of *M. fortuitum*, ATCC 6842, using nitrosoguanidine has resulted in the production of a novel mutant which selectively degrades steroids, as defined herein, to produce compounds I, II, III and IV. This mutant microorganism of *M. fortuitum* has been given the accession number NRRL B-8128, by the Northern Regional Research Laboratory, U.S. Department of Agriculture, Peoria, Ill., U.S.A., where it has been deposited in the permanent collection. A subculture of this microorganism is freely available from this depository by request made thereto. It should be understood that the availability of the culture does not constitute a license to practice the subject invention in derogation of patent rights granted with the subject instrument by governmental action.

The morphology and drug sensitivities of *M. fortuitam*, NRRL B-8128, are indistinguishable from that of the parent *M. fortuitum*, ATCC 6842. Both *M. fortuitum* cultures are acid-fast non-motile, non-sporeforming bacilli belonging to the family Mycobacteriaceae of the order Actinomycetales. According to Runyon's classification (Runyon, E. H. 1959 Med. Clin. North America 43: 273) it is a nonchromogenic group IV mycobacterium, i.e., it grows rapidly at low temperature to produce nonpigmented colonies on relatively simply media.

*M. fortuitum* ATCC 6842 and *M. fortuitum* NRRL B-8128, are clearly distinguishable in their action on steroid molecules. As disclosed above, *M. fortuitum* ATCC 6842 is a non-selective degrader of steroids, whereas *M. fortuitum* NRRL B-8128 is a selective degrader. This property of *M. fortuitum* NRRL B-8128 makes it highly useful, as disclosed herein.

The mutation of *M. fortuitum* ATCC 6842 to give *M. fortuitum* NRRL B-8128 was accomplished by the use of nitroguanidine The details of the procedure are described infra. Though mutation procedures are generally known in the art, there is no known art which teaches or even suggests the type of mutants, if any, which might be obtained by use of the subject mutation procedure. Also, though the mutation and transformation procedures, disclosed herein, are detailed for a Mycobacterium, it should be understood that similar or equivalent procedures can be used with microorganisms of the other genera, as disclosed herein.

The Transformation Process

The selective transformation of the subject invention can be effected in a growing culture of *M. fortuitum* NRRL B-8128 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days. The incubation temperature during the transformation process can range from about 25° C. to about 37° C., with 30° C. being preferred. The contents of the transformation vessel are aerated with sterilized air and agitated to facilitate growth of the microorganism, and, thus, enhance the effectiveness of the transformation process.

Upon completion of the transformation process, as evidenced by thin layer chromatography using silica gel plates (E. Merck, Darmstadt) and a solvent system consisting of 2.3 (by volume) ethyl acetate-cyclohexane, the desired transformed steroids are recovered by means well known in the art. For example, the fermentation (transformation) reaction mixture, including the fermentation liquor and cells, can be extracted with a water-immiscible organic solvent for steroids. Suitable solvents are methylene chloride (preferred), chloroform, carbon tetrachloride, ethylene chloride, trichloroethylene, ether, amyl acetate, benzene and the like.

Alternatively, the fermentation liquor and cells can be first separated by conventional methods, e.g., filtration for centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate vacuum distilled to dryness. The resulting residue containing the desired transformed steroids then can be dissolved in 10% chloroform in Skellysolve B and chromatographed on silica gel, using Skellysolve B (isomeric hexanes) and mixtures thereof with increasing amounts of ethyl acetate as developing solvent. This procedure elutes compounds I, II and III. Compound IV can be eluted with, for example, 5% methanol in ethyl acetate. Crystalline products can be obtained by use of a solvent, for example, ethyl acetate. The desired transformed steroids can also be obtained from the remaining supernatant upon evaporation of the solvent in the supernatant.

Compounds I, II, III and IV, are useful as intermediates in the chemical synthesis of useful steroids. For example, the subject compounds can be converted to starting material for the process disclosed in U.S. Pat. No. 3,880,884 which discloses a process for the total synthesis of useful 19-nor steroids. This conversion to starting material can be done by procedures known in the art, e.g., by oxidation with chromic acid in acetic acid followed by treatment with acetic anhydride and sodium acetate. See Biochem. 2: 1238–1243 and J.A.C.S. 85: 2135–2137.

The following examples are illustrative of the process and products of the subject invention but are not to be construed as limiting. All percentages are by weight and all solvent mixture proportions are by volume unless otherwise noted.

EXAMPLE 1

Preparation of Mutant *M. fortuitum* NRRL B-8128
From *M. fortuitum* ATCC 6842 a. Nitrosoguanidine Mutagenesis

Cells of *M. fortuitum* ATCC 6842 are grown at 28° C. in the following sterile seed medium:

| Nutrient Broth (Difco) | 8 g/liter |
|---|---|
| Yeast Extract | 1 g/liter |
| Sodium Propionate | 0.5 g/liter |
| Distilled Water, q.s. | 1 liter |

The pH is adjusted to 7.0 with 1N NaOH prior to sterilization at 121° C. for 20 minutes.

The cells are grown to a density of about $5 \times 10^8$ per ml, pelleted by centrifugation, and then washed with an equal volume of sterile 0.1 M sodium citrate, pH 5.6. Washed cells are resuspended in the same volume of citrate buffer, a sample removed for titering (cell count), and nitrosoguanidine added to a final concentration of 50 μg/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile minimal salts medium, minus a carbon source, consisting of the following:

| $NH_4NO_3$ | 1.0 g/liter |
|---|---|
| $K_2HPO_4$ | 0.25 g/liter |
| $MgSO_4 \cdot 7H_2O$ | 0.25 g/liter |
| NaCl | 0.005 g/liter |
| $FeSO_4 \cdot 7H_2O$ | 0.001 g/liter |
| Distilled Water, q.s. | 1 liter |

The pH is adjusted to 7.0 with 1N HCl prior to sterilization at 121° C. for 20 minutes. The cells are then plated out to select for mutants.

b. Selection And Isolation Of Mutant M. fortuitum NRRL B-8128.

Mutagenized cells, as described above, are diluted and spread onto plates containing a medium consisting of the following (modified from Fraser and Jerrel. 1963. J. Biol. Chem. 205-295):

| Glycerol | 10.0 g/liter |
|---|---|
| $Na_2HPO_4$ | 8.4 g/liter |
| $KH_2PO_4$ | 4.5 g/liter |
| $NH_4Cl$ | 2.0 g/liter |
| $MgSO_4 \cdot 7H_2O$ | 0.3 g/liter |
| $FeCl_3 \cdot 6H_2O$ | 0.05 g/liter |
| Distilled Water, q.s. | 1 liter |

Agar (15 g/liter) is added, and the medium is autoclaved at 121° C. for 30 minutes and then poured into sterile Petri plates.

Growth on this medium eliminates most nutritional auxotrophs produced by the mutagenesis procedure, e.g. cultures that require vitamins, growth factors, etc. in order to grow on chemically defined medium are eliminated. After incubation at 28° C. for about 7 days, the resulting colonies are replicated to test plates suitable for selecting mutants and then back onto control plates containing the gylcerol-based medium. The test plates are prepared as described by Peterson, G. E., H. L. Lewis and J. R. Davis. 1962. "Preparation of uniform dispersions of cholesterol and other water-insoluble carbon sources in agar media." J. Lipid Research 3:275-276. The minimal salts medium in these plates is as described above in section (a) of Example 1. Agar (15 g/liter), and an appropriate carbon source (1.0 g/liter), such as sitosterol or androstenedione (AD), are added and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of the molten agar plates. In this manner uniform dispersions of water-insoluble carbon sources are obtained which facilitates the preparation of very homogeneous but opaque agar plates.

Colonies which grew on the control plates, but not on test plates containing AD as the sole carbon source, are purified by streaking onto nutrient agar plates. After growth at 28° C., individual clones are picked from the nutrient agar plates with sterile toothpicks and retested by inoculating grided plates containing AD as the carbon source. Purified isolates which still exhibit a phenotype different from the parental culture are then evaluated in shake flasks.

c. Shake Flask Evaluation

Shake flasks (500 ml) contain 100 ml of biotransformation medium consisting of the following ingredients:

| Glycerol | 10.0 g/liter |
|---|---|
| $Na_2HPO_4$ | 8.4 g/liter |
| $KH_2PO_4$ | 4.5 g/liter |
| $NH_4Cl$ | 2.0 g/liter |
| $MgSO_4 \cdot 7H_2O$ | 0.3 g/liter |
| $FeCl_3 \cdot 6H_2O$ | 0.05 g/liter |
| Distilled Water, q.s. | 1 liter |

Soyflour (1 g/liter) is blended into the medium and then sitosterol (10 g/liter) is also blended into the medium. After the flasks are autoclaved for 20 minutes at 121° C., they are cooled to 28° C. and then inoculated with 10 ml of seed growth prepared as follows:

The purified isolates from part (b) are grown on agar slants at 28° C. A loop of cells taken from a slant is used to inoculate a 500-ml flask containing 100 ml of sterile seed medium consisting of the following ingredients:

| Nutrient Broth (Difco) | 8 g/liter |
|---|---|
| Yeast Extract | 1 g/liter |
| Glycerol | 5 g/liter |
| Distilled Water, q.s. | 1 liter |

The pH is adjusted to 7.0 with 1N NaOH prior to autoclaving the flasks at 121° C. for 20 minutes. The seed flasks are incubated at 28° C. for 72 hours.

As disclosed above, 10 ml of seed growth is then used to inoculate each 500-ml flask containing 100 ml of sterile transformation medium. The flasks are then incubated at 28° C. to 30° C. on a rotary shaker and sampled at various intervals. Ten ml samples are removed and extracted by shaking with 3 volumes of methylene chloride. Portions of the extracts are analyzed by thin layer chromatography using silica gel and the solvent system described above, i.e., 2:3 (by volume) ethyl acetatecyclohexane, and by gas-liquid chromatography. Evidence of the presence of compounds I, II, III and IV confirms the selective degradation of sitosterol by the novel mutant produced from the parent *M. fortuitum* ATCC 6842.

EXAMPLE 2

Transformation of Sitosterol to Compounds I, II, III and IV

The medium used is the same as in Example 1c. This medium is sterilized by heating 30 minutes at 121° C., whereupon it is cooled to 30° C. and then inoculated with 10 parts of a seed culture of the mutant mycobacterium *M. fortuitum* NRRL B-8128, prepared as described in Example 1 (c). The inoculated mixture is incubated at 30° C. for 336 hours with agitation to promote submerged growth. Following incubation, the mixture is extracted with methylene chloride. The extract is filtered through diatomaceous earth and the filtrate is vacuum distilled to dryness. The residue is taken up in 10% chloroform in Skellysolve B and chromatographed on silica gel, using Skellysolve B and mixtures thereof with increasing amounts of ethyl acetate as developing solvent. This procedure elutes compounds I, II and III. Compound IV is eluted from the column with 5% methanol in ethyl acetate. The order of elution of the compounds is I → II → III → IV. The $R_f$ values for these compounds on thin layer chromatography (tlc) is as follows (cyclohexane-ethyl acetate; 3:2):

I = 0.37
II = 0.28
III = 0.16
IV = 0.05

Appropriate fractions, as determined by *tlc*, are pooled and evaporated to dryness to afford good yields of compounds I, II, III and IV.

Upon recrystallization from ethyl acetate, compound I, a 1:1 mixture of two epimers, melts at 100°–112° C.;
compound II is an oil;
compound III melts at 122°–124° C.; and
compound IV melts at 148°–150° C.

EXAMPLE 3

By substituting cholesterol for sitosterol in Example 2 there is obtained compounds I, II, III and IV.

EXAMPLE 4

By substituting stigmasterol in Example 2 for sitosterol there is obtained compounds I, II, III and IV.

EXAMPLE 5

By substituting campesterol for sitosterol in Example 2 there is obtained compounds I, II, III and IV.

EXAMPLE 6

By adding a combination of any of the steroids in Examples 2–5, in addition to sitosterol, or in place of sitosterol, in Example 2 there is obtained compounds I, II, III and IV.

EXAMPLE 7

By substituting a sterol-degrading microorganism from the genera Arthrobacter, Bacillus, Brevibacterium, Corynebacterium, Nocardia, Protaminobacter, Serratia, and Streptomyces, in Example 1 for *Mycobacterium fortuitum* ATCC 6842 there are obtained mutant microorganisms which are characterized by their ability to selectively degrade steroids with or without a 17-alkyl side chain of from 2 to 10 carbon atoms, inclusive, and accumulate compounds I, II, III and IV in the fermentation beer.

EXAMPLE 8

By substituting the mutants obtained in Example 7 for *M. fortuitum* NRRL B-8128 in Examples 2–6, there is obtained compounds I, II, III and IV.

EXAMPLE 9

By substituting a sterol-degrading microorganism selected from the group consisting of *Mycobacterium phlei, M. smegmatis, M. rhodochrous, M. mucosum,* and *M. butyricum* for *M. fortuitum* ATCC 6842 in Example 1 there are obtained mutant microorganisms which are characterized by their ability to selectively degrade steroids with or without a 17-alkyl side chain of from 2 to 10 carbon atoms, inclusive, and accumulate compounds I, II, III and IV in the fermentation beer.

EXAMPLE 10

By substituting the mutants obtained in Example 9 for *M. fortuitum* NRRL B-8128 in Examples 2–6, there is obtained compounds I, II, III and IV.

EXAMPLE 11

By substituting a compound selected from the group consisting of androst-4-ene-3,17-dione, androsta-1,4-diene-3,17-dione, dehydroepiandrosterone, and testosterone for sitosterol in Example 2 there is obtained compounds I, II, III and IV.

EXAMPLE 12

By substituting a combination of two or more compounds selected from the group consisting of sitosterol, cholesterol, stigmasterol, androst-4-ene-3,17-dione, androsta-1,4-diene-3,17-dione, dehydroepiandrosterone, and testosterone for sitosterol in Example 2 there is obtained compounds I, II, III and IV.

EXAMPLE 13

By substituting the mutants obtained in Example 7 for *M. fortuitum* NRRL B-8128 in Examples 11 and 12, there is obtained compounds I, II, III and IV.

EXAMPLE 14

By substituting the mutants obtained in Example 9 for *M. fortuitum* NRRL B-8128 in Examples 11 and 12, there is obtained compounds I, II, III and IV.

What is claimed is:

1. A process for preparing a compound of the formula

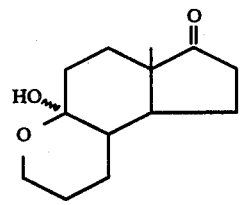

which comprises cultivating *Mycobacterium fortuitum* NRRL B-8128 in an aqueous nutrient medium under aerobic conditions in the presence of a steroid with or without a 17-alkyl side chain containing from 2 to 10 carbon atoms, inclusive.

2. A process, according to claim 1, wherein said steroid is selected from the group consisting of sitosterol, cholesterol, stigmasterol, campesterol, androst-4-ene- 3,17-dione, androsta-1,4-diene-3,17-dione, dehydroepiandrosterone, and testosterone.

3. A process for preparing a compound, as defined in claim 1, which comprises cultivating *Mycobacterium fortuitum* NRRL B-8128 in an aqueous nutrient medium under aerobic conditions in the presence of a mixture of two or more steroids.

4. A process, according to claim 3, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

5. A process for preparing a compound of the formula

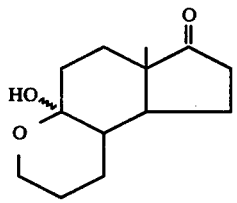

which comprises cultivating a Mycobacteriium mutant which is characterized by its ability to selectively degrade steroids with or without a 17-alkyl side chain of from 2 to 10 carbon atoms, inclusive, and accumulate 3aα-H-4α-[3'-propanol]-7aβ-methylhexahydro-1,5-indandione hemiketal; 3aα-H-4α-[3'-propanal]-5α-hydroxy-7aβ-methylhexahydro-1-indanone hemiacetal; 3aα-H-4α-[3'-propionic acid]-5α-hydroxy-7aβ-methylhexahydro-1-indanone-δ-lactone; and 3aα-H-4α-[3'-propanol]-5α-hydroxy-7aβ-methylhexahydro-1-indanone in the fermentation beer, in an aqueous nutrient medium under aerobic conditions in the presence of a steroid with or without a 17-alkyl side chain containing from 2 to 10 carbon atoms, inclusive.

6. A process, according to claim 5, wherein said mutant microorganism is cultivated in an aqueous nutrient medium under aerobic conditions in the presence of a mixture of two or more steroids.

7. A process, according to claim 5, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

8. A process, according to claim 6, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

9. A process for preparing a compound of the formula

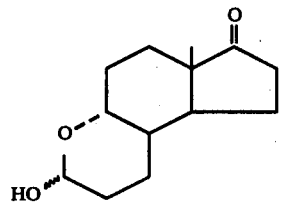

which comprises cultivating *Mycobacterium fortuitum* NRRL B-8128 in an aqueous nutrient medium under aerobic conditions in the presence of a steroid with or without a 17-alkyl side chain containing from 2 to 10 carbon atoms, inclusive.

10. A process, according to claim 9, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

11. A process for preparing a compound, as defined in claim 9, which comprises cultivating *Mycobacterium fortuitum* NRRL B-8128 in an aqueous nutrient medium under aerobic conditions in the presence of a mixture of two or more steroids.

12. A process, according to claim 11, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

13. A process for preparing a compound of the formula

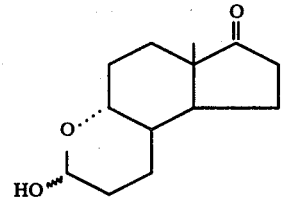

which comprises cultivating a Mycobacterium mutant which is characterized by its ability to selectively degrade steroids with or without a 17-alkyl side chain of from 2 to 10 carbon atoms, inclusive, and accumulate 3aα-H-4α-[3'-propanol]-7aβ-methylhexahydro-1,5-indandione hemiketal; 3aα-H-4α-[3'-propanal]-5α-hydroxy-7aβ-methylhexahydro-1-indanone hemiacetal; 3aα-H-4α-[3'-propionic acid]-5α-hydroxy-7aβ-methylhexahydro-1-indanone-δ-lactone; and 3aα-H-4α-[3'-propanol]-5α-hydroxy-7aβ-methylhexahydro-1-indanone in the fermentation beer, in an aqueous nutrient medium under aerobic conditions in the presence of a steroid with or without a 17-alkyl side chain containing from 2 to 10 carbon atoms, inclusive.

14. A process, according to claim 13, wherein said mutant microorganism is cultivated in an aqueous nutrient medium under aerobic conditions in the presence of a mixture of two or more steroids.

15. A process, according to claim 13, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

16. A process, according to claim 14, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

17. A process for preparing a compound of the formula

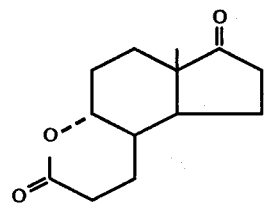

which comprises cultivating *Mycobacterium fortuitum* NRRL B-8128 in an aqueous nutrient medium under aerobic conditions in the presence of a steroid with or without a 17-alkyl side chain containing from 2 to 10 carbon atoms, inclusive.

18. A process, according to claim 17, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

19. A process for preparing a compound, as defined in claim 17, which comprises cultivating *Mycobacterium fortuitum* NRRL B-8128 in an aqueous nutrient medium under aerobic conditions in the presence of a mixture of two or more steroids.

20. A process, according to claim 19, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

21. A process for preparing a compound of the formula

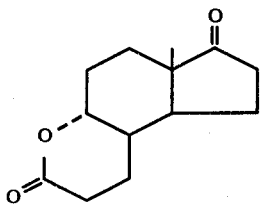

which comprises cultivating a *Mycobacterium* mutant which is characterized by its ability to selectively degrade steroids with or without a 17-alkyl side chain of from 2 to 10 carbon atoms, inclusive, and accumulate 3aα-H-4α-[3'-propanol]-7aβ-methylhexahydro-1,5-indandione hemiketal; 3aα-H-4α-[3'-propanal]-5α-hydroxy-7aβ-methylhexahydro-1-indanone hemiacetal; 3aα-H-4α-[3'-propionic acid]-5α-hydroxy-7aβ-methylhexahydro-1-indanone-δ-lactone; and 3aα-H-4α-[3'-propanol]-5α-hydroxy-7aβ-methylhexahydro-1-indanone in the fermentation beer, in an aqueous nutrient medium under aerobic conditions in the presence of a steroid with or without a 17-alkyl side chain containing from 2 to 10 carbon atoms, inclusive.

22. A process, according to claim 21, wherein said mutant microorganism is cultivated in an aqueous nutrient medium under aerobic conditions in the presence of a mixture of two or more steroids.

23. A process, according to claim 21, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

24. A process, according to claim 22, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

25. A process for preparing a compound of the formula

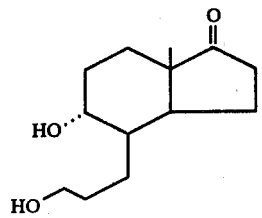

which comprises cultivating *Mycobacterium fortuitum* NRRL B-8128 in an aqueous nutrient medium under aerobic conditions in the presence of a steroid with or without a 17-alkyl side chain containing from 2 to 10 carbon atoms, inclusive.

26. A process, according to claim 25, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

27. A process for preparing a compound, as defined in claim 25, which comprises cultivating *Mycobacterium fortuitum* NRRL B-8128 in an aqueous nutrient medium under aerobic conditions in the presence of a mixture of two or more steroids.

28. A process, according to claim 27, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

29. A process for preparing a compound of the formula

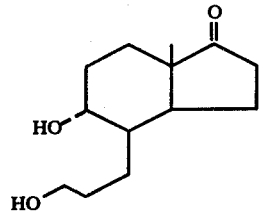

which comprises cultivating a *Mycobacterium* mutant which is characterized by its ability to selectively degrade steroids with or without a 17-alkyl side chain of from 2 to 10 carbon atoms, inclusive, and accumulate 3aα-H-4α-[3'-propanol]-7aβ-methylhexahydro-1,5-indandione hemiketal; 3aα-H-4α-[3'-propanal]-5α-hydroxy-7aβ-methylhexahydro-1-indanone hemiacetal; 3aα-H-4α-[3'-propionic acid]-5α-hydroxy-7aβ-methylhexahydro-1-indanone-δ-lactone; and 3aα-H-4α-[3'-propanol]-5α-hydroxy-7aβ-methylhexahydro-1-indanone in the fermentation beer, in an aqueous nutrient medium under aerobic conditions in the presence of a steroid with or without a 17-alkyl side chain containing from 2 to 10 carbon atoms, inclusive.

30. A process, according to claim 29, wherein said mutant microorganism is cultivated in an aqueous nutrient medium under aerobic conditions in the presence of a mixture of two or more steroids.

31. A process, according to claim 29, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

32. A process, according to claim 30, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

33. A process for preparing a fermentation beer containing compounds of the formulae

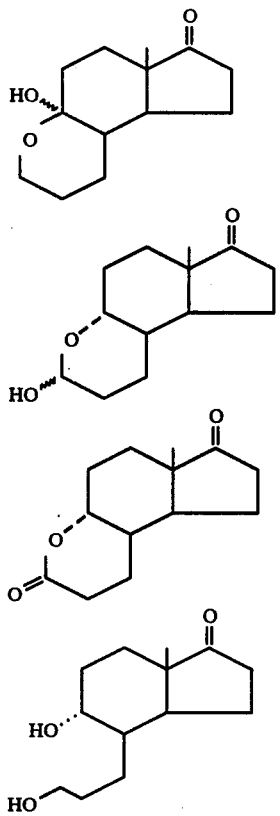

which comprises cultivating *Mycobacterium fortuitum* NRRL B-8128 in an aqueous medium under aerobic conditions in the presence of a steroid with or without a 17-alkyl side chain containing from 2 to 10 carbon atoms, inclusive.

34. A process, according to claim 33, wherein said steroid is selected from the group consisting of sitosterol, cholesterol, stigmasterol, campesterol, androst-4-ene-3,17-dione, androsta-1,4-diene, 3,17-dione, dehydroepiandrosterone, and testosterone.

35. A process for preparing a fermentation beer, as defined in claim 33, which comprises cultivating *Mycobacterium fortuitum* NRRL B-8128 in an aqueous nutrient medium under aerobic conditions in the presence of a mixture of two or more steroids.

36. A process, according to claim 35, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

37. A process for preparing a fermentation beer containing compounds of the formulae

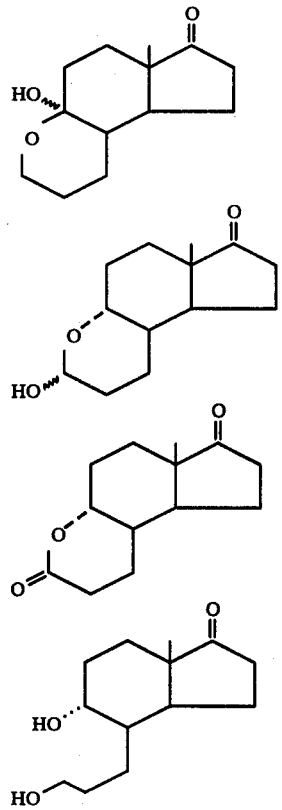

which comprises cultivating a *Mycobacterium* mutant which is characterized by its ability to selectively degrade steroids with or without a 17-alkyl side chain of from 2 to 10 carbon atoms, inclusive, and accumulate 3aα-H-4α-[3'-propanol]-7aβ-methylhexahydro-1,5-indandione hemiketal; 3aα-H-4α-[3'-propanal]-5α-hydroxy-7aβ-methylhexahydro-1-indanone hemiacetal; 3aα-H-4α-[3'-propionic acid]-5α-hydroxy-7aβ-methylhexahydro-1-indanone-δ-lactone; and 3aα-H-4α-[3'-propanol]-5α-hydroxy-7aβ-methylhexahydro-1-indanone in the fermentation beer, in an aqueous nutrient medium under aerobic conditions in the presence of a steroid with or without a 17-alkyl side chain containing from 2 to 10 carbon atoms, inclusive.

38. A process, according to claim 37, wherein said mutant microorganism is cultivated in an aqueous nutrient medium under aerobic conditions in the presence of a mixture of two or more steroids.

39. A process, according to claim 37, wherein said steroid is selected from the group consisting of sitosterol, cholesterol, stigmasterol, campesterol, androst-4-ene-3,17-dione, androsta-1,4-diene-3,17-dione, dehydroepiandrosterone, and testosterone.

40. A process, according to claim 38, wherein said steroid mixture is selected from the group consisting of sitosterol, cholesterol, stigmasterol, campesterol, androst-4-ene-3,17-dione, androsta-1,4-diene-3,17-dione, dehydroepiandrosterone, and testosterone.

* * * * *

UNITED STATES PATENT OFFICE
CERTIFICATE OF CORRECTION

Patent No. 4,042,459    Dated August 16, 1977

Inventor(s) John C. Knight and Merle G. Wovcha

It is certified that error appears in the above-identified patent and that said Letters Patent are hereby corrected as shown below:

Column 1, line 10, for "17ketosteroids" read -- 17-ketosteroids --; line 16, for "be" read -- by --; line 31, for "7α-methyl:" read -- 7α-methyl- --. Column 3, lines 18-19, for "*fortuitam*" read -- *fortuitum* --; line 38, for "nitroguanidine" read -- nitrosoguanidine. --. Column 4, line 21, for "2.3" read -- 2:3 --. Column 5, line 44, for "205-295" read -- 205: 291-295 --. Column 6, line 63, for "acetatecyclohexane" read -- acetate-cyclohexane --. Column 9, line 25, claim 5, for "Mycobacteriium" read -- *Mycobacterium* --. Column 13, line 47, claim 34, for "androsta-1,4-diene," read -- androsta-1,4-diene- --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks